(12) United States Patent
Halm

(10) Patent No.: US 7,824,052 B1
(45) Date of Patent: Nov. 2, 2010

(54) FOOT CONTROLLED LIGHT OPERATION

(76) Inventor: Gary V. Halm, 821 N. Fielder, Arlington, TX (US) 76012

( * ) Notice: Subject to any disclaimer, the term of this patent is extended or adjusted under 35 U.S.C. 154(b) by 62 days.

(21) Appl. No.: 12/075,617

(22) Filed: Mar. 12, 2008

Related U.S. Application Data

(60) Provisional application No. 60/895,173, filed on Mar. 16, 2007.

(51) Int. Cl.
 *F21V 21/084* (2006.01)
(52) U.S. Cl. .................. 362/105; 362/276; 362/802
(58) Field of Classification Search .................. 362/103, 362/105–107, 276, 802, 804
 See application file for complete search history.

(56) References Cited

U.S. PATENT DOCUMENTS

| | | | |
|---|---|---|---|
| 2,990,765 A * | 7/1961 | Winzenburg ................ | 396/14 |
| 4,195,918 A | 4/1980 | Freche et al. | |
| 4,866,229 A | 9/1989 | Scharfenberg | |
| 4,956,752 A | 9/1990 | Foglietti | |
| 4,975,937 A | 12/1990 | Horton et al. | |
| 5,331,357 A | 7/1994 | Cooley et al. | |
| 5,526,245 A | 6/1996 | Davis et al. | |
| 5,637,863 A | 6/1997 | Sanborn et al. | |
| 5,667,291 A | 9/1997 | Caplan et al. | |
| 5,704,707 A | 1/1998 | Gebelein et al. | |
| 6,091,546 A | 7/2000 | Spitzer | |
| 6,101,038 A | 8/2000 | Hebert et al. | |
| 6,114,812 A | 9/2000 | Lee | |
| 6,169,377 B1 | 1/2001 | Bryde et al. | |
| 6,348,859 B1 | 2/2002 | Baker | |
| 6,377,401 B1 | 4/2002 | Bartlett | |
| 6,720,870 B2 | 4/2004 | Morse | |
| 7,008,074 B1 | 3/2006 | Halm | |
| 2003/0067769 A1 | 4/2003 | Gilpin | |

FOREIGN PATENT DOCUMENTS

WO   WO 00/17849   3/2000

* cited by examiner

*Primary Examiner*—Jason Moon Han
(74) *Attorney, Agent, or Firm*—Law Office of William Gustavson, PC

(57) ABSTRACT

A hands-free dental or surgical light system (100) is disclosed which allows the dentist or surgeon to dim and turn a light (12) on and off by simply pressing pedals on a foot operated assembly (106). First and second receivers (102, 104) are mounted in a power pack (28) usually worn about the waist. First and second foot operated transmitters (112, 114) are turned on and off or activated with the foot of the operator. The first transmitter (112) and receiver (102) operate to toggle the light (12) between the dim and brightened states while the second transmitter (114) and receiver (104) operate to toggle the light on and off.

1 Claim, 4 Drawing Sheets

FOOT CONTROLLED LIGHT OPERATION

CROSS REFERENCE TO RELATED APPLICATIONS

This application claims priority from Provisional Patent Application Ser. No. 60/895,173 filed Mar. 16, 2007.

TECHNICAL FIELD

This invention relates to dental and surgical procedures, and in particular to assisting those procedures with proper lighting.

BACKGROUND OF THE INVENTION

A dentist or surgeon often has need of a strong concentrated light to illuminate an area being treated. For example, in dentistry, the patient's mouth must be well illuminated. However, many materials used in dentistry are cured by exposure to light, particularly ultraviolet or blue light. Therefore, the dentist may wish to reduce the intensity of the light at certain times to prevent the curing from proceeding too quickly. Commercial lights are available which mount on the dentist's forehead and are operated through a fiber-optic cable from a tabletop light source and control. The light can be switched on or off, or dimmed at a tabletop control. However, this is often inconvenient for the dentist as it requires the dentist to stop patient treatment, turn the control to set the desired light condition, and then turn back to the patient.

SUMMARY OF THE INVENTION

In accordance with one aspect of the present invention, a light source is positioned on the head of an operator. A first receiver is positioned proximate the light source. A power supply is provided to power the light source. A first foot operated transmitter is located remotely from the first receiver, with the first receiver being activated when the operator presses on a first foot pedal of the first transmitter to send a signal to the first receiver to activate the light source.

In accordance with another aspect of the present invention, a second receiver is positioned proximate the light source. The first receiver can cause the light source to toggle between bright and dim when the first receiver is activated by the first transmitter. The second receiver can cause the light source to toggle on and off when the second receiver is activated by a second foot operated transmitter.

BRIEF DESCRIPTION OF THE DRAWINGS

For a more complete understanding of the present invention and the advantages thereof, reference is now made to the following Detailed Description, taken in conjunction with the accompanying Drawings, in which.

DETAILED DESCRIPTION

Figure 1:
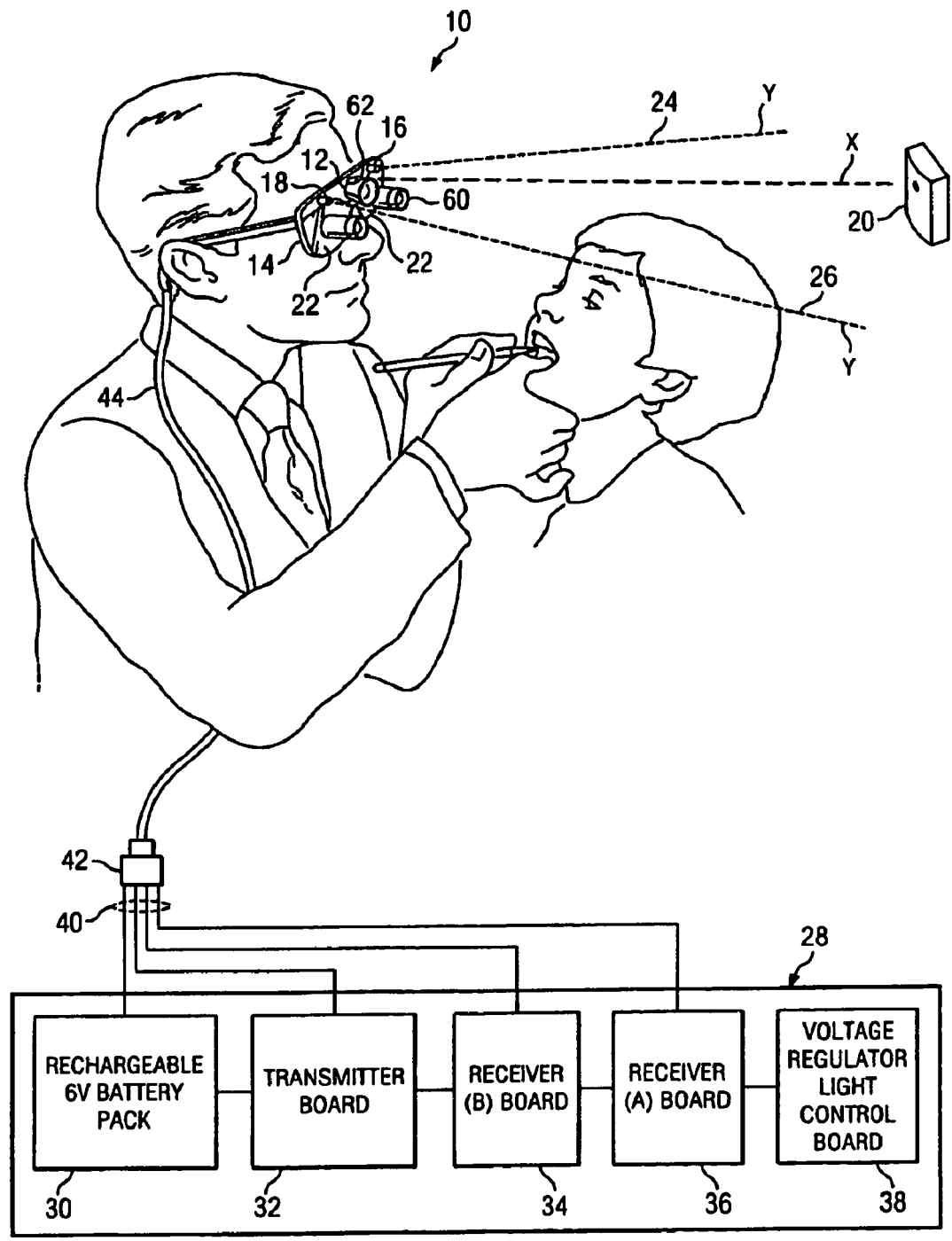
FIG. 1 is a schematic view of a first embodiment of the present invention.
Figure 2:
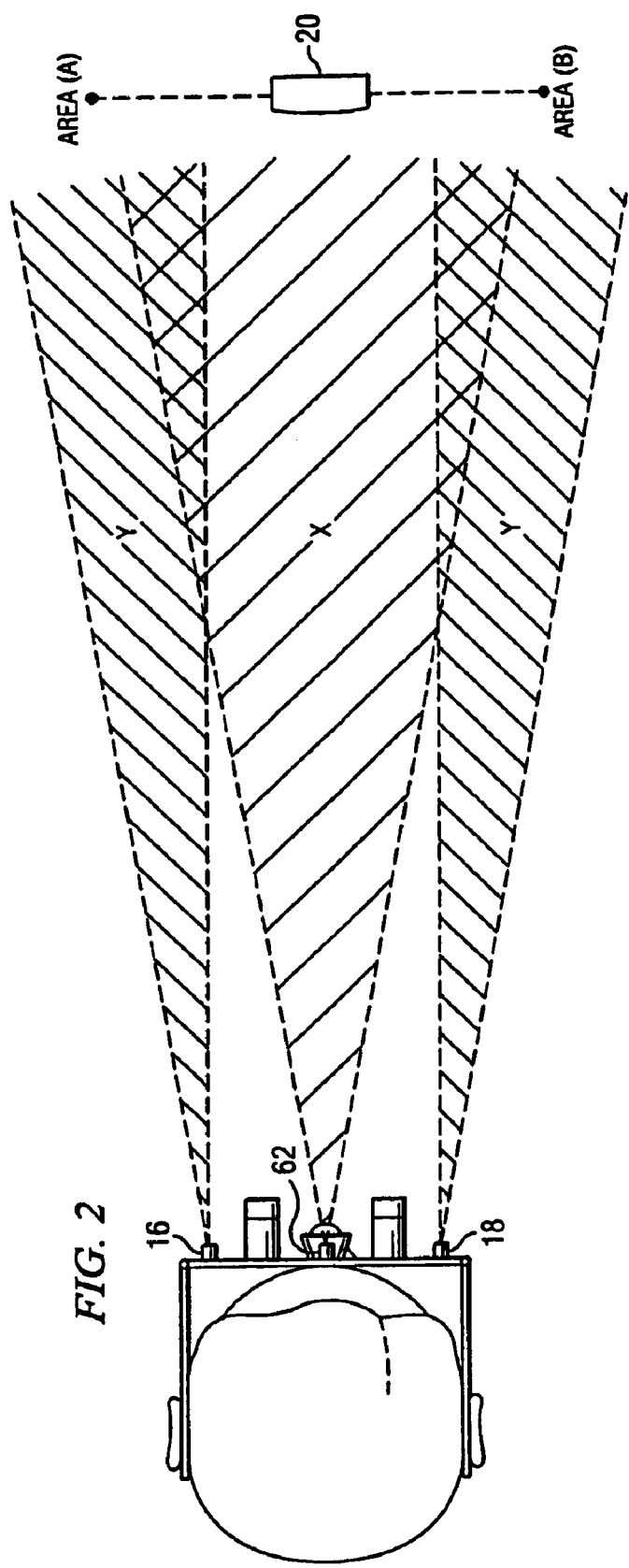
FIG. 2 is a schematic view of the embodiment illustrating the infrared path.
Figure 3:
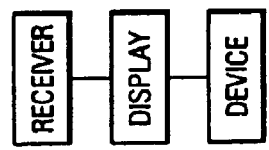
FIG. 3 is a flowchart of operation of a modification with an auxiliary device being powered up or down.

With reference now to the drawings, a hands-free dental and surgical light system 10 forming a first embodiment of the present invention will be described. The light system 10 includes a light 12 mounted to a pair of optical loupes or safety glasses 14 worn by the dentist or surgeon, which commonly include magnifying loupes 60. As will be described in greater detail, the operator can turn the light 12 on and off and dim or brighten the light 12 by simply moving their head so that either a first infrared sensitive receiver such as infrared sensitive switch 16 or a second infrared sensitive receiver such as infrared sensitive switch 18 points to a remotely located infrared source 20 to activate the selected switch. This allows the operator to dim and turn the light on and off without using their hands or being distracted from the particular operation being undertaken.

With reference to FIG. 1, the light system 10 can be seen to include the light 12 mounted on the glasses 14 between the lenses 22 so as to be best aligned with the operator's vision. The light 12 can be an incandescent bulb (such as a halogen bulb), or a series of LEDs. For dental work, if LEDs are used, light 12 can be toggled between a bright mode with all white LEDs and a dimmed mode with a combination of colored LEDs (minus the blue light spectrum). The curing of dental materials is often accomplished with blue or ultraviolet light. The first infrared sensitive switch 16 is mounted to glasses 14 on one side of the light 12 and oriented so that it is sensitive to infrared light entering the switch along path 24 which is at an angle relative to the line of vision of the operator. The second infrared sensitive switch 18 is mounted on the glasses 14 on the other side of the light 12 and is similarly oriented to receive infrared signals along path 26 at a second angle relative to the line of vision of the operator. A transmitter 62 can be mounted on the glasses 14 near the light 12 to transmit control signals, as described hereinafter. The light 12, switches 16 and 18 and transmitter 62 can be mounted on a head band, rather than glasses 14, if desired.

A power pack 28 is worn by the operator, preferably on their belt or around their neck, and contains a rechargeable battery pack 30, preferably between seven and ten volts with a charge of approximately 30 watt hours. The power pack 28 also includes a transmitter board 32, a first receiver board 34 associated with the first infrared sensitive switch 16 and a second receiver board 36 associated with the second infrared sensitive switch. Preferably, a voltage regulator control board 38 is also provided to regulate the voltage from the battery pack 28 to the light 12. A cable 40 extends from the power pack 28 to one side of plug 42. The other side of plug 42 connects to a cable 44 extending to the glasses 14. This allows the operator to unplug the power pack 28 from the glasses 14.

To dim and turn light 12 on and off, the operator need only move their head to point a selected one of the infrared sensitive switches 16 or 18 toward the remotely mounted infrared source 20 to activate the selected switch. The remotely mounted infrared source 20 is preferably mounted high on a wall or on the ceiling or to the sides of the operating area so that the operator does not activate a switch inadvertently while performing the particular operation on the patient. If the operator wishes to dim the light 12, or return it to full brightness from the dimmed state, the operator can simply move their head to aim the first infrared sensitive switch 16 at the infrared source 20 and the light will be dimmed or restored to full brightness by activation of the switch 16 and the appropriate circuitry on first receiver board 34. Similarly, if the operator wishes light 12 to be turned on or off, the operator moves their head to aim the second infrared sensitive switch 18 at the infrared source 20, which turns the light 20 on or off when the second infrared sensitive switch 18 is activated in cooperation with the circuitry on second receiver board 36. The infrared source 20 can be a simple infrared source if the only desired functions are to control light 12. However, infrared source 20 is preferably a transponder source when the transmitter 62 is used in order to control other functions, as discussed hereinafter.

As can be understood, the light system 10 provides complete portability and mobility to the operator. The operator is not bound by wires or fiber-optic cables to a fixed power supply or controls. The light 12 can be switched on and off and dimmed without the hands of the operator or any staff assistance, eliminating the risk of broken sterility in the operating field.

When powered by a seven to ten volt rechargeable battery pack 28, the output of the battery pack is usually higher than desired, for sensitive bulbs or LEDs for a short period of time when fully charged. Thus, voltage regulation is recommended to limit over voltage, which has been known to cause light bulb filament failure. Voltage regulation is also important if light source 12 consists of white and red LED's. These LEDs require regulation to limit current through the LED.

The dimming of the light 12 is accomplished by first receiver board 34 when the first infrared sensitive switch 16 is activated by either controlling the voltage regulator supply board 38 to reduce the applied voltage or by reducing current to the light 12. When the light 12 consists of white and colored (without the blue spectrum) LEDs, dimming can be achieved by reducing current flow to the white LEDs while the colored LEDs are left at full brightness, as only blue light, around 465 nm, affects light cured materials, and the colored LEDs therefore have no effect on the materials.

The operator may use the transmitter 62 for control of other devices, such as overhead lights, curing lights for composites, electro-surgical units, X-ray view boxes and the like. All these devices can be controlled hands-free. Additionally, transmitter 62 can operate relays to control a patient's chair position and control other nonelectrical devices. Preferably, the transmitter 62 transmits an infrared signal at a frequency (X) different than that received by the switches 16 and 18(Y) to insure a lack of interference. Use of discrete subchannel frequencies is necessary to keep reflections from causing unwanted operation of the light. Reliability is near 100%. When using transmitter 62, the remote infrared source 20 is a transponder to receive signals of frequency X from the transmitter 62, with the transponder responding with signals of frequency Y.

Figure 4:
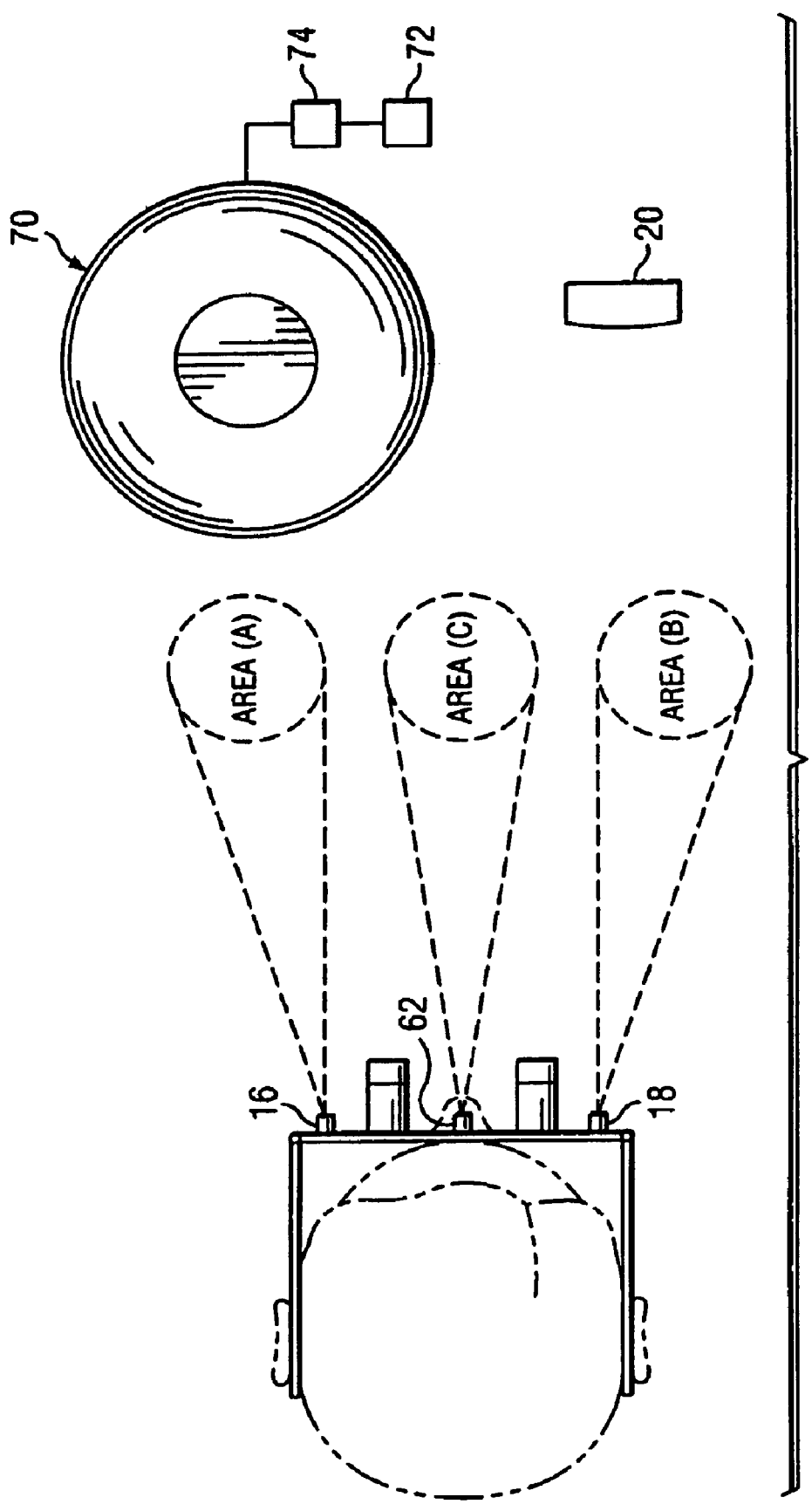
FIG. 4 is an illustration of the control of an auxiliary device, specifically an overhead light.

With reference to FIG. 4, transmitter 62 can be used to control a traditional, focused, operatory overhead light 70. At the beginning of a dental procedure, for example, position of the patient is set and the overhead light 70 is focused and aimed into the oral cavity of the patient. Currently, the doctor or assistant must manually operate the light 70 even though gloved and observing aseptic or sterile techniques.

The transmitter 62 can be used to switch the overhead light 70 on and off, either by sending a signal to the transponder in remote infrared source 20, or to a dedicated overhead light receiver 72 controlling the overhead light 70 through a toggle switch 74. In either design, the overhead light 70 is thus controlled by the head position of the operator.

Any electrical device can be toggled on or off, or varied in operation, in a similar manner. By using the transmitter 62 with overhead light 70, three different areas have been defined, area A to dim or brighten the light 12, area B to turn the light 12 on or off, and area C to control the overhead light 70. The head of the operator need only be aimed such that the specific area chosen covers infrared source 20 with the transponder or receiver 72 to operate the desired function. Clearly, additional devices can be operated by simply providing additional receivers associated with the devices and creating other unique head aiming position areas to operate the specific devices.

The use of the light system 10 can be expanded beyond medical applications, and can be used by anyone to operate any device without manual control. Examples include use by those wheel chair bound or having impaired mobility, or those confined to a particular operating station by their job, such as a switchboard operator or plant operations monitor.

Among the benefits of the light system 10 is higher productivity and speed while maintaining a sterile field. This allows the operator much longer working time when using light sensitive materials in the dimmed mode. Energy savings are realized as the light need only be on when needed. An unlimited variety of electrical devices can be controlled by the system 10, including chair position. The light and power supply stays with the operator so the costs of equipping multiple treatment rooms is eliminated.

Figure 5:
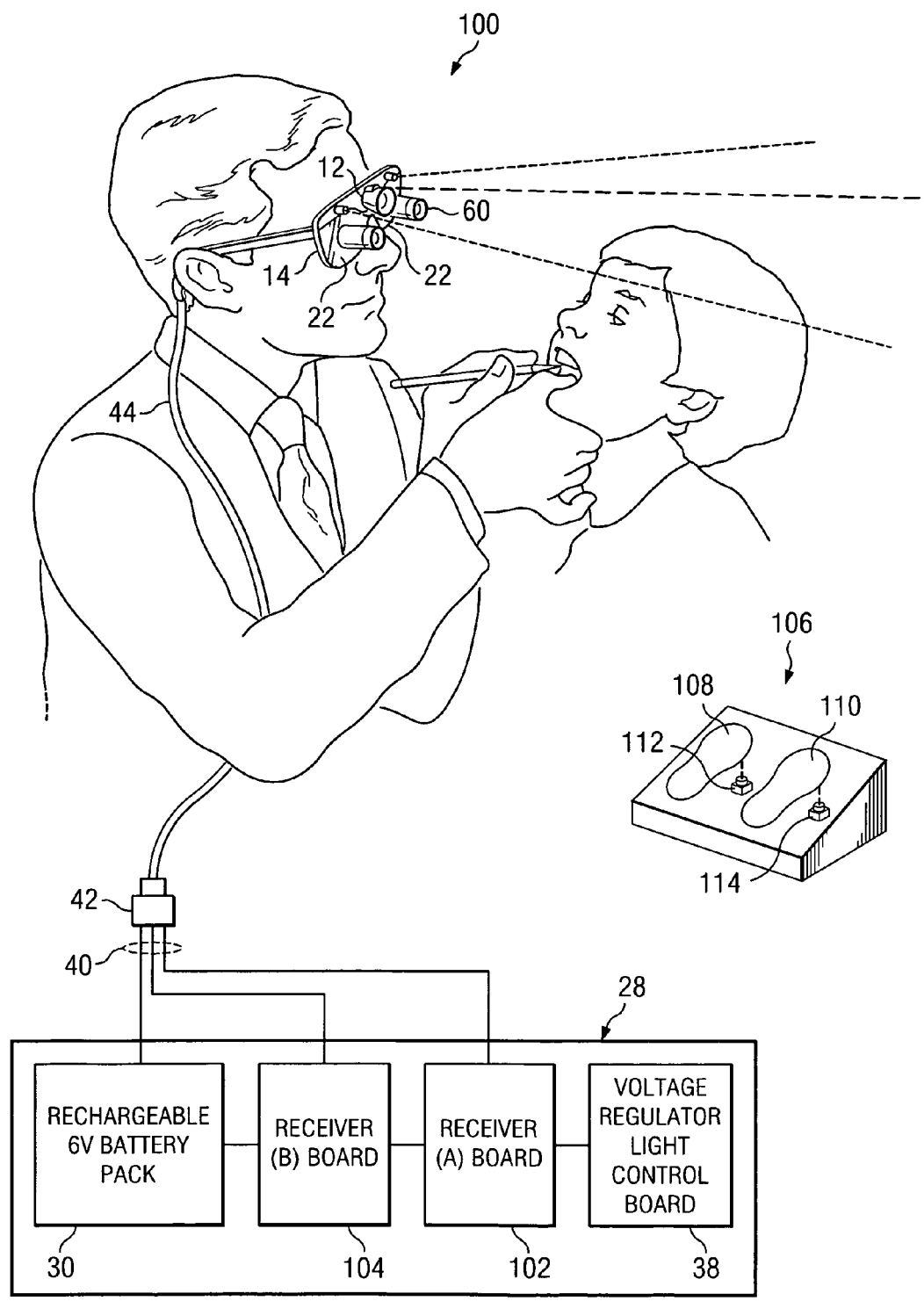
FIG. 5 is a schematic of a second embodiment of the present invention.

With reference now to FIG. 5, a hands-free dental and surgical light system 100 forming a second embodiment of the present invention will be described. Light system 100 also employs light 12 mounted to a pair of optical loupes or safety glasses 14 worn by the dentist or surgeon. Light system 100 also uses power pack 28, typically worn by the operator about the waist, containing rechargeable battery pack 30 to power the light 12. However, the power pack 28 has a first receiver 102 that is designed to receive an electro-magnetic signal, such as a radio or infrared signal, to dim or brighten the light 12. The power pack 28 also has a second receiver 104 that is designed to receive an electro-magnetic signal, such as a radio or infrared signal, to turn the light 12 on and off. The light system 100 also includes a foot operated assembly 106, preferably having two separate foot pedals 108 and 110, that generates the electro-magnetic signals received by first and second receivers 102 and 104 to brighten and dim light 12 and to turn light 12 on and off.

The foot operated assembly 106 preferably includes a first transmitter 112 activated by pushing on the foot pedal 108 and a second transmitter 114 activated by pushing on the foot pedal 110. Activation of the first transmitter 112 transmits a signal to the first receiver 102 to toggle the light 12 between the bright and dimmed states. In other words, if the light 12 is in the bright state, pushing on the foot pedal 108 will toggle the light 12 to the dimmed state. Pushing on the foot pedal 108 again will toggle the light 12 back to the bright state. Activation of the second transmitter 114 transmits a signal to the second receiver 104 to toggle the light 12 between the on and off states. In other words, if the light 12 is on, pushing on the foot pedal 110 will toggle the light 12 off. Pushing on the foot pedal 110 again will toggle the light 12 back on. The foot operated assembly 106 can be powered by a battery pack therein, or connected to an external power source. Preferably, the foot operated assembly 106 is placed on the floor in a position where the operator can easily press the foot pedals 108 and 110 with their foot to control light operation. Clearly, the function of foot pedals 108 and 110 can be accomplished using simple switches on assembly 106, or their function can be combined into a single foot pedal with multiple positions.

By using a foot operated assembly 106 with no physical connection to the light 12 or power pack 28, the same advantages of freedom of movement, ease of operation and hands-free operation as discussed above with light system 10 are realized.

The transmitters 112 and 114 and receivers 102 and 104 can communicate using any suitable electro-magnetic signal system, such as a 2.4 Ghz transmission, preferably encoded, infra red signals, spread spectrum signals, Blue Tooth, and the like. Preferably, an encoded signal is used so that transmitters 112 and 114 will only activate the receivers 102 and 104 they are paired with, and not receivers in an adjacent operating theater or other location.

As with first receiver board 34, first receiver 102 can dim light 12 by either controlling the voltage regulator supply board 38 to reduce the applied voltage or by reducing current to the light 12. When the light 12 consists of white and colored (without the blue spectrum) LEDs, dimming can be achieved by reducing current flow to the white LEDs while the colored LEDs are left at full brightness.

While several embodiments of the invention have been illustrated in the accompanying drawings and described in the foregoing Detailed Description, it will be understood that the invention is not limited to the embodiments disclosed, but is capable of numerous rearrangements, modifications and substitutions of parts and elements without departing from the spirit and scope of the invention.

The invention claimed is:

1. An apparatus, comprising:
   a light source positioned on the head of an operator;
   a first receiver positioned proximate the light source, the first receiver operating the light source upon activation of the first receiver;
   a second receiver positioned proximate the light source, the second receiver operating the light source upon activation of the second receiver;
   a power supply to power the light source; and
   a first foot operated transmitter operating with an encoded radio signal located remotely from the light source and first receiver, said first foot operated transmitter having no physical connection with the light source and first receiver, the first receiver activated by the first foot operated transmitter;
   a second foot operated transmitter operating with an encoded radio signal located remotely from the light source and second receiver, said second foot operated transmitter having no physical connection with the light source and second receiver, the second receiver activated by the second foot operated transmitter;
   the light source being dimmed when the first receiver is activated by the first foot operated transmitter and restored to full brightness when the first receiver is again activated by the first foot operated transmitter and the light source being turned off when the second receiver is activated by the second foot operated transmitter and turned on when the second receiver is again activated by the second foot operated transmitter.

* * * * *